US008047981B2

(12) United States Patent
Rao et al.

(10) Patent No.: US 8,047,981 B2
(45) Date of Patent: Nov. 1, 2011

(54) MEDICAL SLINGS

(75) Inventors: Doreen Rao, Watertown, MA (US);
Alfred P. Intoccia, Jr., Amherst, NH (US); Bard Parkinson, Marlborough, MA (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 183 days.

(21) Appl. No.: 10/641,170

(22) Filed: Aug. 14, 2003

(65) Prior Publication Data
US 2005/0038451 A1 Feb. 17, 2005

(51) Int. Cl.
*A61F 2/00* (2006.01)
*A61B 17/08* (2006.01)
(52) U.S. Cl. .......................................... 600/37; 606/151
(58) Field of Classification Search ................... 606/151, 606/30, 74; 600/30, 37; 623/23.72, 23.6, 623/23.74; 128/885; 24/16 PB
See application file for complete search history.

(56) References Cited

U.S. PATENT DOCUMENTS

| 5,919,232 | A | * | 7/1999 | Chaffringeon et al. ........ 424/423 |
| 6,110,101 | A | * | 8/2000 | Tihon et al. ...................... 600/37 |
| 6,197,036 | B1 | | 3/2001 | Tripp et al. |
| 6,447,551 | B1 | | 9/2002 | Goldmann |
| 6,953,428 | B2 | * | 10/2005 | Gellman et al. ................. 600/29 |
| 7,083,568 | B2 | | 8/2006 | Neisz et al. |
| 2004/0005353 | A1 | | 1/2004 | Lopez-Berestein et al. |
| 2004/0006353 | A1 | | 1/2004 | Bosley, Jr. et al. |
| 2004/0144395 | A1 | | 7/2004 | Evans et al. |
| 2004/0231678 | A1 | * | 11/2004 | Fierro ............................ 128/885 |
| 2006/0058578 | A1 | * | 3/2006 | Browning ........................ 600/37 |

FOREIGN PATENT DOCUMENTS

| EP | 0774240 | 5/1997 |
| WO | WO-03/086205 A2 | 10/2003 |
| WO | WO-03/105727 | 12/2003 |
| WO | WO-2004/004600 A1 | 1/2004 |

* cited by examiner

*Primary Examiner* — Corrine M McDermott
*Assistant Examiner* — Melissa Ryckman
(74) *Attorney, Agent, or Firm* — Bingham McCutchen LLP

(57) ABSTRACT

A sling including a material having a plurality of edges. At least one of the edges of the material has a pattern of projections.

42 Claims, 5 Drawing Sheets

MEDICAL SLINGS

TECHNICAL FIELD

This invention generally relates to a surgical sling, such as a mid-urethral sling, methods of making such a sling, kits including such a sling, and methods of treating or reinforcing a damaged, prolapsed, weakened or herniated portion of a patient's body using such a sling.

BACKGROUND OF THE INVENTION

Surgical prosthetic mesh has been used to treat or reinforce tissues or organs which have been damaged, prolapsed, weakened, or otherwise herniated, such as in the conditions rectocele, cystocele, enterocele, vaginal prolapse, and protocele, for example. A prolapse refers to the slipping of an organ, or organ part, from its normal position. For example, a prolapse of the rectum refers to the protrusion of the rectum through the anus. Rectocele is the prolapse of the rectum into the perineum. A prolapse of the uterus refers to the falling of the uterus into the vagina due to stretching and laxity of its supporting structures. Vaginal vault prolapse refers to the prolapse of the cephalad extreme of the vaginal wall toward, through, and beyond the introitus. Cystocele (i.e., vesicocele) is a hernia formed by the downward and backward displacement of the urinary bladder toward the vaginal orifice, due most commonly to weakening of the musculature during childbirth. However, any abnormal descent of the anterior vaginal wall and bladder base at rest or with strain is considered cystocele. Enterocele is a hernia of the intestine, though the term is also used to refer specifically to herniation of the pelvic peritoneum through the rectouterine pouch (i.e., posterior vaginal, rectovaginal, cul-de-sac, or Douglas' pouch hernia).

Stress urinary incontinence (SUI), which primarily affects women, is a condition that is also successfully treated using surgical slings. Stress urinary incontinence is generally caused by two conditions that may occur independently or in combination, namely, intrinsic sphincter deficiency (ISD) and hypermobility. In ISD, the urinary sphincter valve, located within the urethra, fails to close properly, causing urine to leak out of the urethra during stressful actions. Hypermobility is a condition in which the pelvic floor is distended, weakened or damaged, causing the bladder neck and proximal urethra to rotate and descend in response to increases in intra-abdominal pressure (e.g., due to sneezing, coughing, straining, etc.), resulting in insufficient response time to promote urethral closure and, consequently, in urine leakage and/or flow.

Biological factors that may affect hypermobility include: poor endopelvic fascia muscle tone (from age or limited activity), endopelvic fascia muscle stretch/tear from trauma (e.g. childbirth), endopelvic fascia/arcus tendenious (muscle/ligament) separation (lateral defect), hormone deficiency (estrogen), concombinant defects (cystocele, enterocele, ureteral prolapse), and vaginal prolapse. Traditional treatment methods include urethra or bladder neck stabilization slings in which a sling is placed under the urethra or bladder neck to provide a platform preventing over distention. An emerging alternative treatment is the placement of a mid-urethral sling. Such a sling placement takes advantage of the hypermobility condition by providing a fulcrum about which the urethra and bladder neck will rotate and provide a "urethral kink" to assist normal urethral closure.

Slings are traditionally placed under the urethra or bladder neck to provide a urethral platform limiting endopelvic fascia drop while providing compression to the urethral sphincter to improve coaptation. The mid-urethral placement location provides mechanical stability to a less moveable anatomical structure. Bladder neck slings have traditionally been affixed in the desired location using a bone anchoring method. Mid-urethral slings, being placed in a low mobility area, have demonstrated the effectiveness of an anchorless approach. Recognizing that minimal tension, if any, is necessary, a physician need only place the sling under the mid-urethra secured through the endopelvic fascia to permanently secure the sling in position. The sling permits immediate tissue security through the mesh openings and mesh cavities to initially maintain sling stabilization. As healing occurs, the endopelvic fascia and rectus fascia tissue re-establish vascularity and regrow into and around the knit pattern of the mesh. The sling in this procedure provides a fulcrum about which the pelvic floor will drop (taking advantage of the hypermobility condition of the patient) and a urethral "kink" or higher resistance to obstruct urine flow during high stress conditions.

Problems associated with the use of mid-urethral slings include a tendency to move once positioned in the body because the slings are not anchored well. Furthermore, mid-urethral slings are known in the art to have a tendency to become stretched or misshapen during surgical placement. These problems can result in the sling not being anchored appropriately to the tissue when placed in the body, thus reducing the sling's functional effectiveness. Thus, there is a need to produce a sling which lessens the chance of the sling shifting once positioned in the body, there is also a need to prevent the sling from becoming misshapen during handling.

SUMMARY OF THE INVENTION

The invention, in various embodiments, is directed to a surgical sling, wherein at least a portion of one of the edges of the sling has a plurality of projections, e.g., a preselected pattern of projections; methods of making such a sling; medical kits including such a sling; and methods of treating a damaged, weakened, sagging, herniated or prolapsed portion of a patient's body using such a sling. The benefits of a sling having at least a portion of an edge having a plurality of projections include rapid revascularization and tissue ingrowth when placed in contact with tissue.

In one aspect, the invention is directed to a surgical sling for implantation in the tissues of a patient. The sling includes a first edge, at least a portion of the first edge having a pattern of projections that extend laterally from the edge, wherein the projections anchor the sling when the sling is implanted in the patients tissues. In one embodiment, the pattern of projections are preselected. In another embodiment, the sling has a series of apertures extending from the first side to the second side. In another embodiment, at least one of the sling's first and/or second sides has an irregular surface. The irregular surface can be provided by, for example, one or more ridges, projections, depressions or a combination thereof. In another embodiment, the sling includes a foam material. In a further embodiment, the sling includes a tensioning-device. In some embodiments, the sling is at least partially enclosed by a sleeve.

In another aspect, the invention includes a method of making a sling, the method including forming on a portion of an edge of the sling a pattern of projections that extend laterally from the edge. Preferably, the pattern is not randomly determinable, but instead preselected. In one embodiment, the method includes providing a sling dimensioned appropriately for inserting into an anatomical site within the body. In another embodiment, the method includes forming a series of apertures extending from a first side to a second side. The method may also include forming an irregular surface on the first and/or second sides of the sling by introducing, for example, one or more ridges, projections, depressions or combinations thereof. The method of making the sling may also include sterilizing the sling material so that the sling is suitable for use in various medical applications.

The sling of the invention can be made, for example, of a synthetic material such as nylon, polyethylene, polyester, polypropylene, fluoropolymers or a co-polymer thereof, or, for example, of a mammalian tissue material such as bovine, porcine, equine, human cadaveric or engineered tissue. In one embodiment, the material of the sling includes a combination of synthetic and mammalian tissue materials.

Preferably, the sling of the invention is shaped for placement within a patient's body. Such shapes include, for example, rectangular, substantially rectangular, octagonal, hexagonal, trapezoidal, elliptical, or any other shape that is suitable to the sling's intended placement location within the body.

In a further aspect, the invention involves a method of treating a damaged portion of a patient's body using a sling as described above. The sling material may be implanted to treat female urinary incontinence according to transobturator, transvaginal, transabdominal, or a combination of such procedures. For example, the method may be employed to treat a patient with stress urinary incontinence.

BRIEF DESCRIPTION OF THE DRAWINGS

In the drawings, like reference characters generally refer to the same parts throughout the different views. The drawings are not necessarily to scale, but rather illustrate the principles of the invention.

DESCRIPTION

The invention, in one illustrative embodiment, relates to a surgical sling having a portion of an edge, including a plurality of projections. Advantages of the sling of the invention include anchoring firmly in tissue following surgical placement, permitting rapid revascularization and tissue ingrowth when placed in contact with a tissue, such as urethral or vaginal tissue, and retaining its shape during surgical placement. The projections of the invention include lateral protrusions that are also introduced into the material forming the sling, e.g., on any or all edges, sides or surfaces of the sheet of material. Optionally, the invention also includes the formation of a plurality of projections in the sling. Preferably, the projections are formed to create a pattern. More preferably, the pattern of projections is chosen before they are introduced into the material forming the sling, i.e., the pattern of projections are preselected. The pattern can include any combination of projections.

Figure 1:
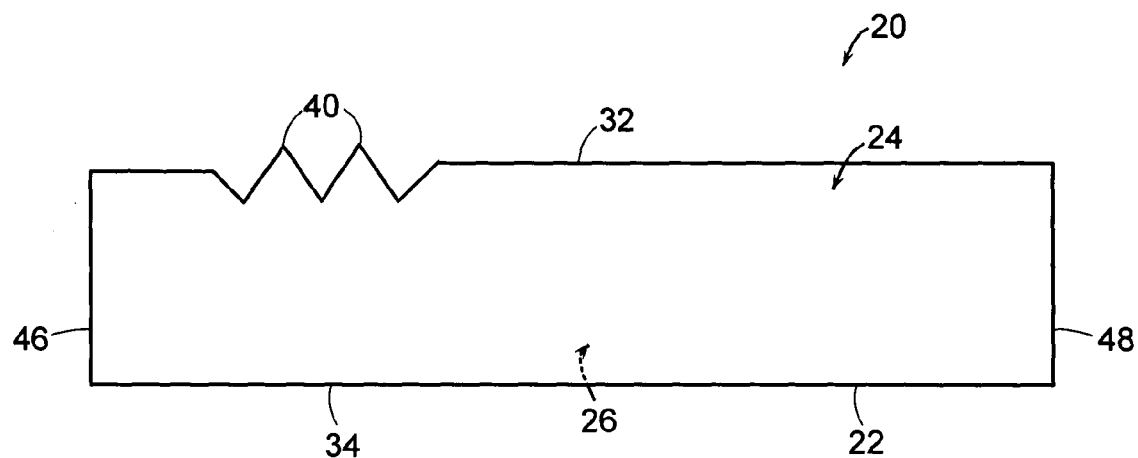
FIG. 1 depicts a top view of a sling according to an illustrative embodiment of the invention.

FIG. 1 depicts a top view of a sling according to an illustrative embodiment of the invention. As shown, the sling 20 can be made of a material 22 such as a sheet of material and includes a first side 24 and an opposing second side 26. The sling has a first edge 32, a second edge 34, a third edge 46 and a fourth edge 48. The material 22 has along a portion of at least one of its edges, 32, 34, 46 or 48, a plurality of projections 40. Optionally, the plurality of projections form a pattern of projections. The sling 20 is preferably in the range of about 20 to about 50 cm in length, and about 1 to about 3 cm wide, though larger or smaller slings 20 are contemplated to suit the size of the patient and/or the application. The thickness of the material 22, i.e., the distance between the first side 24 and the second side 26, may be uniform over the entire sling 20 or the thickness may vary at one or more different locations. Preferably, the thickness of the material 22 ranges from about 0.05 to about 0.2 cm, and is typically about 0.08 cm. As illustrated in FIG. 1, the sling 20 is rectangular, or substantially rectangular in shape. However, in alternative embodiments, the sling may have a shape (e.g., trapezoidal, hexagonal, octagonal or elliptical) suitable for its intended location at an anatomical site within a patient's body.

Figure 2:
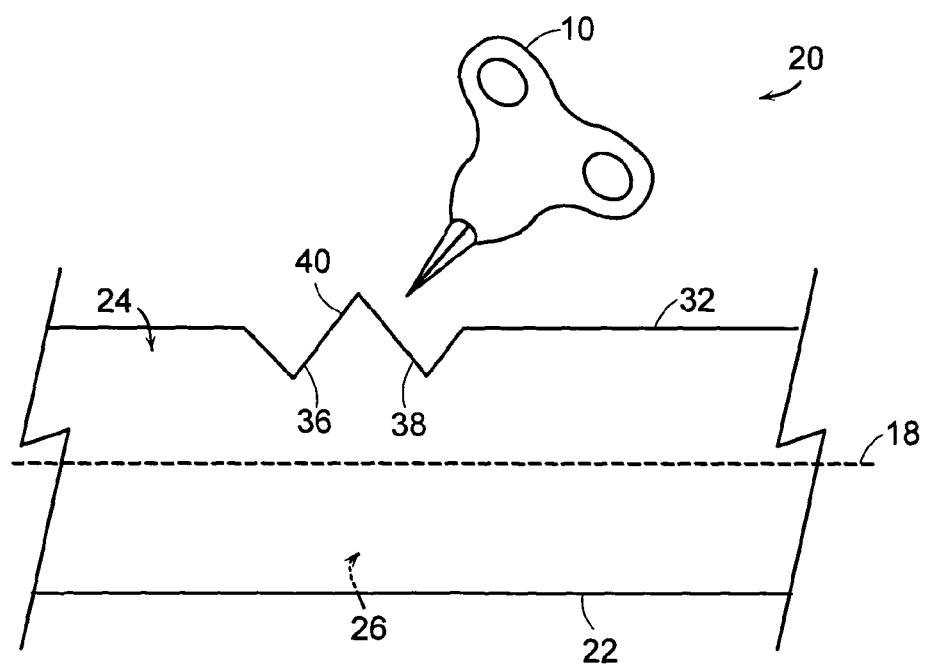
FIG. 2 depicts another top view of a sling according to an illustrative embodiment of the invention.

FIG. 2 depicts another top view of a sling according to an illustrative embodiment of the invention. In this illustrative embodiment, at least one projection 40 extends laterally from at least one of the edges 32, 34, 46 or 48, preferably the first edge 32 or the second edge 34, or a combination of the first edge 32 and the second edge 34, of the sling 20. According to the illustrative embodiment, the projections 40 form a preselected pattern of projections. The pattern of projections 40 of the sling 20 may be formed, for example, by cutting, molding, stamping, punching, melting, or other suitable manufacturing process. The projections of the invention, preferably, do not include random projections, which can result, for example, when a material is cut, chopped or torn. Typically, the resultant frayed edges of the sling material includes a substantially random pattern of thread ends. As illustrated in FIG. 2, the projections 40 may be formed by cutting the material with a pair of scissors 10 to form the V-shaped projection 40. Preferably, the cutting extends inwardly at an angle relative to the first edge 32, towards a midline 18 of the sling material. According to some embodiments, the cut extends beyond the midline 18. The second side 38 of the V-shaped projection 40 is made by cutting inwardly at another angle relative to the first edge 32 of sling 20. The steps performed as described above are repeated to create a pattern of projections 40. The projections 40 are created along at least a portion of at least one edge 32, 34, 46 or 48 of the sling 20 and may extend at least partially from the first side 24 to the opposing second side 26 of the sling 20 or, alternatively, at least partially from the second side 26 to the first side 24.

Figure 3:
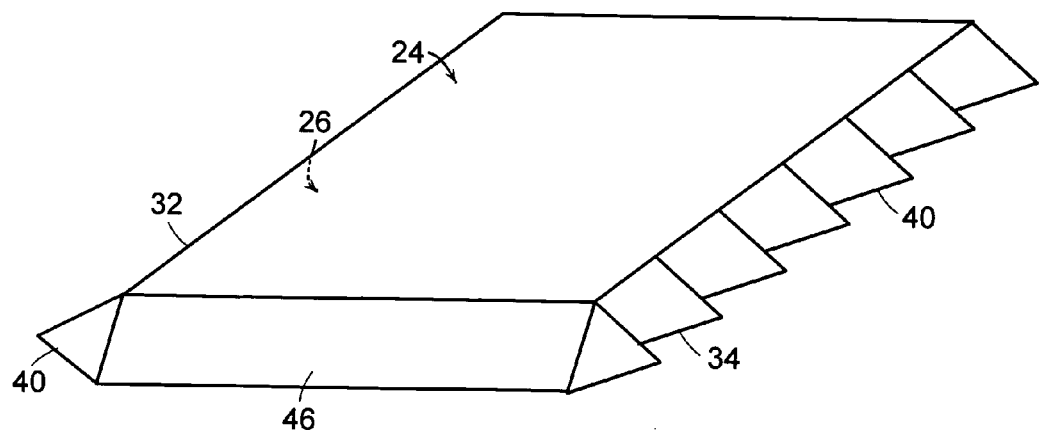
FIG. 3 depicts a perspective end view of a sling according to an illustrative embodiment of the invention.

FIG. 3 depicts a perspective end view of a sling according to an illustrative embodiment of the invention. In this illustrative embodiment, the projections 40 on one or more edges 32, 34, 46, or 48 of sling 20 are substantially V-shaped. However, according to other illustrative embodiments of the invention, the projections 40 may have any suitable shape, such as round, square, rectangle, U-shaped, L-shaped or crescent-shaped. Additionally, the projections 40 may be a combination of different shapes. In one embodiment, a portion of the projection 40 is enlarged relative to the other parts of the projection.

Figure 4:
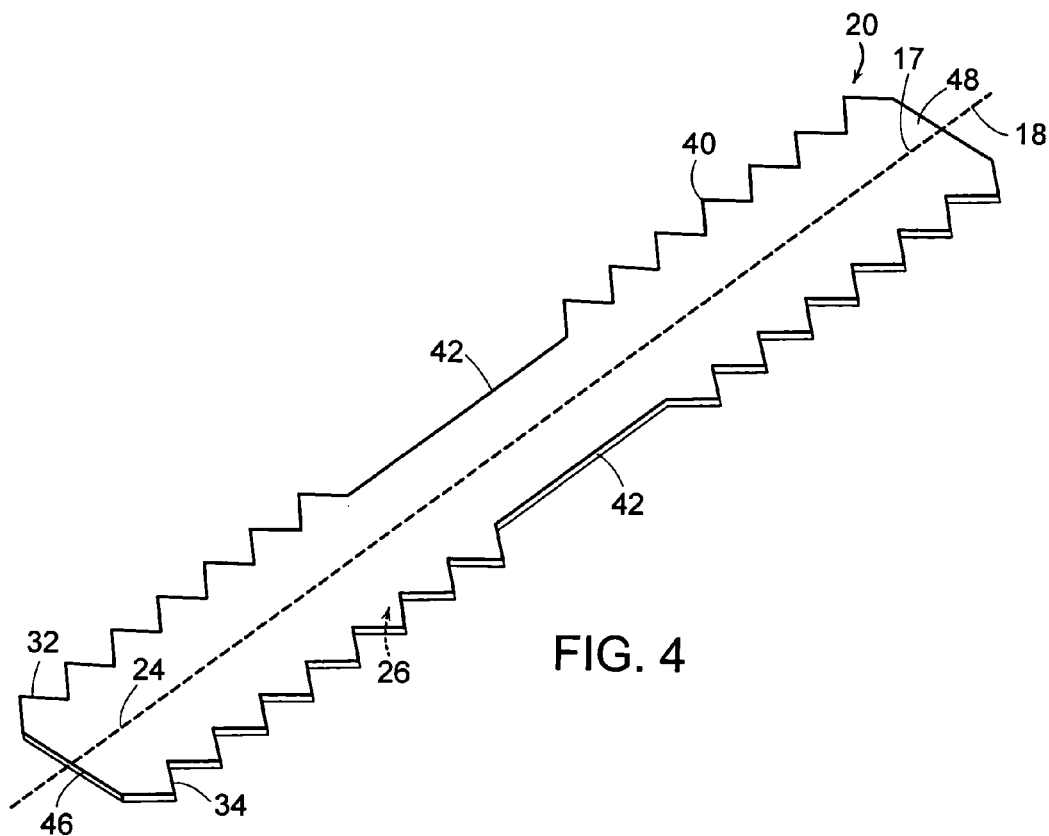
FIG. 4 depicts a perspective top view of a sling according to an illustrative embodiment of the invention.

Preferably, the portion of the sling 20, which is in close proximity to the urethra and anterior vaginal wall, does not contain any projections 40. FIG. 4 depicts a perspective top view of a sling 20 according to such an embodiment of the invention. As shown, the sling 20 of FIG. 4 has a portion of each edge 32 and 34 having projections 40 and a portion of each edge 32 and 34 on both sides of the midpoint of the long axis 17 of the sling 20 being free of projections 40.

Figure 5:
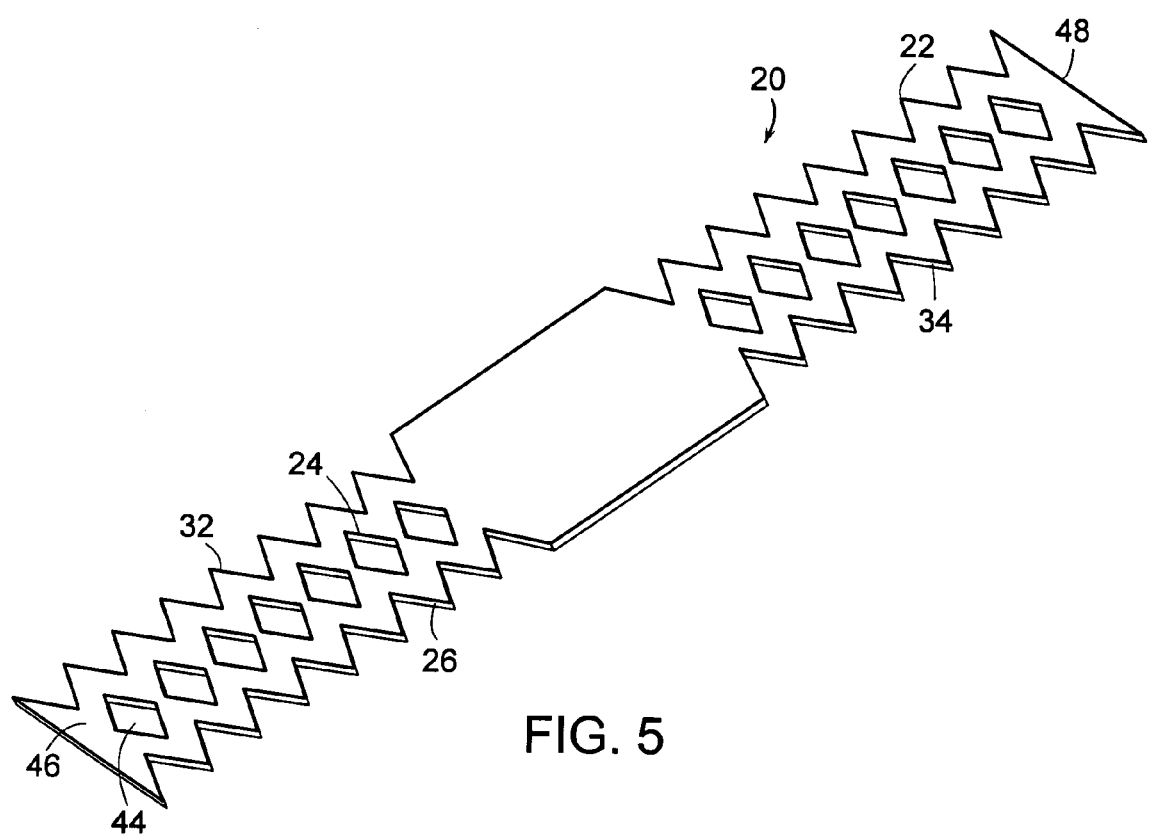
FIG. 5 depicts a perspective top view of a sling according to an illustrative embodiment of the invention.

FIG. 5 depicts a perspective top view of the sling 20 according to a further illustrative embodiment of the invention. In any embodiment described herein, the material 22 of the sling 20 may be imperforate or the material 22 may be perforated. In the embodiment of FIG. 5, the material 22, including a plurality of apertures 44, which may extend partially, or completely, from the first side 24 to the second side 26 or from the second side 26 to the first side 24 of the material 22. In another illustrative, the apertures 44 may extend along a portion of the first side 24, and/or along a portion of the second side 26 of the material 22. The apertures 44 can be any suitable shape and size. The shape of the apertures 44 may be, for example, round, square, diamond-shaped (as shown in FIG. 6), or triangular.

Figure 6:
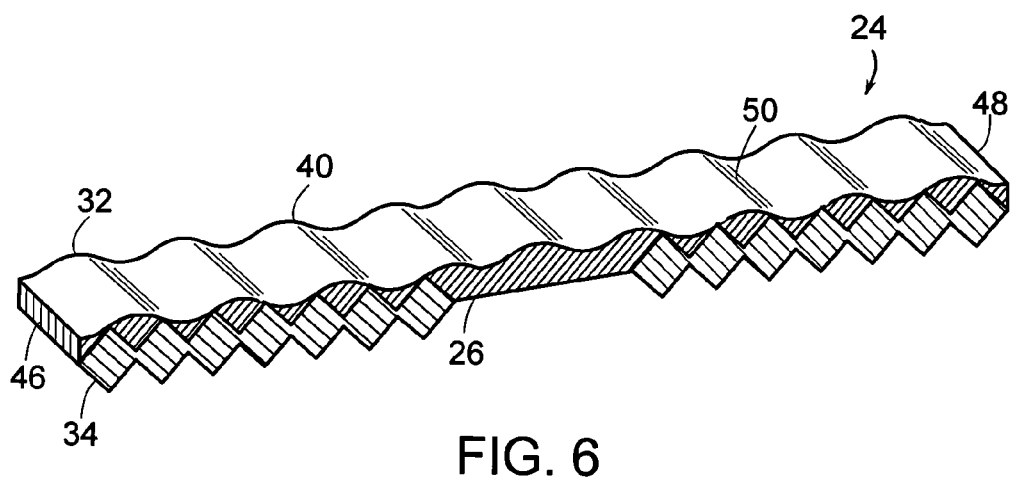
FIG. 6 depicts a perspective side view of a sling according to an illustrative embodiment of the invention.

FIG. 6 depicts a perspective side view of an alternative illustrative embodiment of the sling 20 wherein at least one of the sides 24 and 26 are textured. In this particular illustrative embodiment, the surface of the first side 24 of sling 20 has an irregular-surface 50. The irregular-surface 50 acts to enhance tissue growth into the sling 20 and also aids in stabilization of the sling 20 in the tissue through frictional forces. The irregular-surface 50 may be formed from, for example, a ridge, a depression, a projection, or a combination thereof. In one example, the irregular-surface 50 is provided by a series of ridges disposed across the width of the sling 20, from first edge 32 to second edge 34. In an alternative illustrative embodiment, a loop or series of loops are introduced into at least a portion of the first side 24 of sling 20. In such an embodiment, the loops may be cut to create loose fiber ends extending from at least a portion of the first side 24 of sling 20. In another alternative embodiment, the irregular surface is introduced by embossing the side 24. Alternatively, the choice of sling material may define the irregular surface 50 of a side. For example, the material may be irregular because of changes in thickness through variations in fiber diameter and/or changes in knit or weave density, or because of other variations in material conditions.

Figure 7:
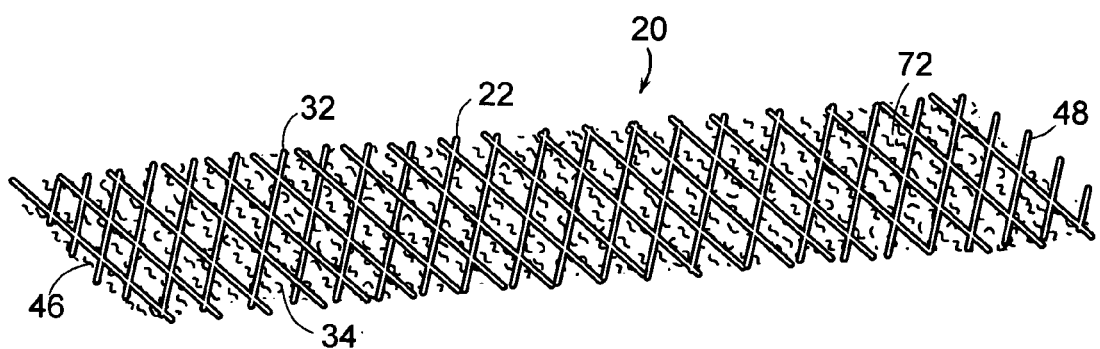
FIG. 7 depicts a top view of a sling according to an illustrative embodiment of the invention.

FIG. 7 is a perspective top view of another illustrative embodiment of the sling 20. In this illustrative embodiment, the sling 20 includes a foam material 72. The foam material 72 can be disposed, for example, into an interior aperture or apertures in the material 22 as illustrated in FIG. 5, or otherwise embedded into the sling 20. Alternatively, the foam material 72 can be disposed onto one or both of the sides 24 and 26. The foam material 72 can be adhered to the material 22, for example, by thermal bonding, and can be configured to absorb a drug prior to implantation. The foam material 72 may also be configured to release the drug at a desired rate in the body, providing an extended release. Exemplary drugs include neomycin, sulfa drugs, antimicrobials, and antibiotics. The foam material 72 may be manufactured from, for example, polyvinyl acetate (PVA), polyurethane, silicone, polyester, polyethylene, etc.

Figure 8:
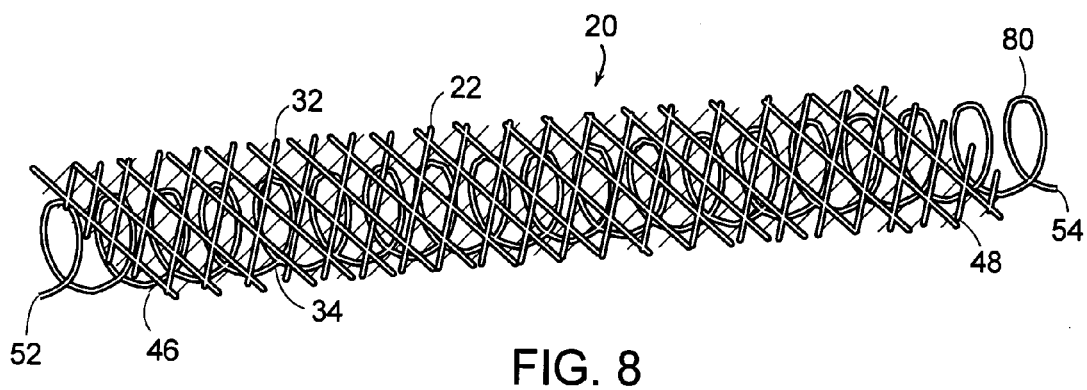
FIG. 8 depicts a top view of a sling according to an illustrative embodiment of the invention.

FIG. 8 is a top view of a further illustrative embodiment of sling 20, including a tensioning device 80. The tensioning device 80 limits the stretch of the sling 20, aids in the application of even tension along the length of the sling 20, and aids in preventing the sling 20 from becoming misshapen. The tension device 80, for example, may be a coil, illustrated in FIG. 8, embedded in the material 22 of the sling 20. The coil 80 includes a first end 52 and a second end 54. During placement of the sling 20 in the body, tension is applied to the first end 52 and second end 54 of the coil 80, or to both the first end 52 and second end 54 of the coil 80. The length of and the number of turns in the coil 80 limits the amount of stretch in the sling 20 that can occur by tension applied to the sling 20. Accordingly, the tensioning device 80 prevents the sling 20 from being deformed beyond the point where the elasticity of the sling permits the sling 20 to return to its shape before tension was applied to the sling 20. If this over-tensioning is not prevented, the physician will have difficulty adjusting the sling tension for proper sling placement and function. Other tensioning devices known in the art can be used, for example, as described in U.S. patent application Ser. No. 10/641,942 entitled Medical Slings, inventor Chu, filed on even day herewith, the entire contents of which is incorporated by reference herein.

Figure 9:
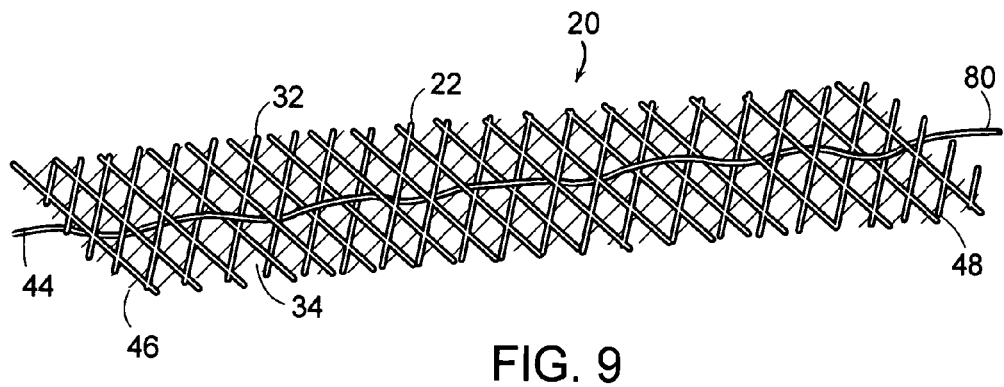
FIG. 9 depicts a top view of a sling according to an illustrative embodiment of the invention.

FIG. 9 depicts another alternative embodiment of the sling 20 where the tensioning device 80 is formed as one or more strands 44, that parallel the long axis 17 of the material 22 and are embedded in or intertwined with the material 22. In the illustrative embodiment of FIG. 9, the strand 44 is formed, for example, from a suture material. The sling 20 is tensioned by pulling on one or both ends of the strand 44. The tensioning-device 80 can be made from, for example, resorbable or non-resorbable suture material. For example, resorbable suture material can be made from PLA (poly lactic acid), PGA (poly glycolic acid), PLLA (poly-l-lactic acid), or other resorbable polymers. The non-resorbable materials are typically polypropylene (PP), polybutester or other non-resorbable polymers. The tensioning device 80 can be embedded into or intertwined with the sling 20 by, for example, weaving, molding or bonding the tensioning device 80 to the sling 20, or by otherwise physically or chemically attaching it to the sling 20. Alternatively, to limit the stretch of the sling 20, the sling 20 can be surrounded by, or enclosed within, a sleeve or envelope.

The material of sling 20 may be fabricated from any of a number of biocompatible materials such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials include polyglycolic acid (PGA), polylactic acid, and other suitable absorbable synthetic materials. A suitable PGA material is available under the trade designation DEXON, from TYCO (Exeter, N.H.). Other suitable polymeric, non-polymeric synthetic materials or their combination may be employed in accordance with the invention. In one embodiment, the synthetic material is porous.

The sling material may, alternatively, be derived from mammalian tissue(s). The mammalian tissue source may be, for example, human, human cadaveric, or tissue-engineered human tissue. The mammalian tissue may alternatively be derived from an animal source such as porcine, ovine, bovine, and equine tissue sources.

The sling 20 can be formed from one or more materials or portions of the sling can be formed from one or more materials. For example, a portion of the sling 20 having projections can be composed of a non-absorbable material and a portion of the sling, such as the central portion of the sling 20, can be formed from a absorbable or biodegradable material. Exemplary biodegradable materials include, but are not limited to, human dermis and decellularized animal tissue. Additionally, exemplary biodegradable polymers include, but are not limited to, polylactic acid, polyglycolic acid and copolymers and mixtures thereof such as poly(L-lactide) (PLLA), poly(D,L-lactide) (PLA); polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL); polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly (amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polyethylene oxide, hydroxypropylmethylcellulose, polysaccharides such as hyaluronic acid, chitosan and regenerate cellulose, and proteins such as gelatin and collagen, and mixtures and copolymers thereof.

The sling material may also be made of a combination of mammalian tissue and synthetic material. Such combinations may also include materials that include both synthetic material and animal cells that are processed to render the tissue non-antigenic. These processes may result in an acellular product and may include cross-linking of the collagen within the tissue. In one embodiment, at least a portion of the sling 20, which contacts the patient's tissue, comprises a synthetic material that is substantially smooth.

The sling 20 in some configurations is made of a non-wettable material such as a polypropylene, polyethylene, polyester, polytetrafluoroethylene, TYVEK available from DuPont, Pa., MYLAR available from DuPont, Pa., or copolymers thereof. Polytetrafluoroethylene, which is suitable for use in accordance with the present invention, is available from DuPont (Wilmington, Del., under the trade designation TEFLON). Such non-wettable materials do not take up any liquids, for example, therapeutic agents in solution.

To permit therapeutic agents to bond or absorb to these non-wettable material sides, the sling 20 may be treated with a substance that is wettable such as, for example, a wettable coating composition. The wettable coating composition may be a synthetic coating (e.g., polyvinylpyrrlidone or PVP), a natural coating (e.g., collagen) or a physically absorbent material (e.g., sponge comprising cellulose or open celled polyurethane). The wettable coating composition may be hydrophilic. Suitable hydrophilic coatings may be water soluble and include, for example, such coatings available under the trade designations Hydroplus and Hydropass. Similarly, a hydrophobic coating may be employed on one or more surfaces of the sling 20. Suitable hydrophobic coatings that may be employed in accordance with the invention include but are not limited to polytetrafluoroethylene, silicon, and Pyrelene.

Therapeutic agents may also be employed with sling 20. For example, the hydrophilic coating and the therapeutic agent are mixed to form a single coating. Alternatively, the therapeutic agents may be compressed into the material of the sling, rather than being applied as a coating.

The therapeutic agents can be, for example, hydrophilic or hydrophobic. Hydrophilic drugs that may be employed in accordance with the invention include oxybutynin chloride, lidocaine, ketorolac, ketorolac tromethamine, which is available under the trade designation Toradol from Roche Pharmaceuticals (Nutley, N.J.) and hyoscyamine sulfate which is available under the trade designation CYTOSPAZ from Polymedica (Woburn, Mass.), for example. Suitable hydrophobic drugs include but are not limited to ibuprofen, ketoprofen, and diclofenac. The drug can be mixed with the coating and applied with the coating. Where the bonding between the coatings and drugs is weak, the drug that is absorbed will readily release to be delivered to the sides it contacts. Alternatively, a stronger bonding affinity may provide a slower timed release of the drug.

Where the coating applied to the surface of the sling 20 has an ionic charge, drugs comprising a complementary charge will bond to the coating when the coating and the drug are exposed to one another. The strength of any bonding will impact how readily the drug is released from the sling 20. Where the ionic bonding between the coating and the drug is weak, the drug will release more readily. In embodiments where rapid drug release is desirable, covalent bonding between the side coating and the drug should be avoided.

In general, the therapeutic agent for use in connection with the present invention can be any pharmaceutically acceptable therapeutic agent. Preferred therapeutic agents include anti-inflammatory agents, analgesic agents, local anesthetic agents, antispasmodic agents, and combinations thereof.

Anti-inflammatory agents include steroidal and non-steroidal anti-inflammatory agents. Examples of non-steroidal anti-inflammatory drugs, include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethlythiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocalne hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocalne, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenylpropylamine, tropenzile, trospium chloride, xenytropium bromide, and pharmaceutically acceptable salts thereof.

Two particularly preferred therapeutic agents for the practice of the present invention are (a) ketorolac and pharmaceutically acceptable salts thereof (e.g., the tromethamine salt thereof, sold under the commercial name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropan®).

The amount of the therapeutic agent present in the polymeric matrix is an amount effective to reduce the pain or discomfort associated with the medical device. Typically, the therapeutic agent is present in a polymeric matrix in a range from about 0.1% to about 30% by weight of the polymeric matrix (including 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% and ranges between any two of these points, for instance, 0.1-10%, 10-20% and 20-30%, etc.). Where the oxybutynin chloride and ketorolac tromethamine are used a range of 2-20% is typical, more typically 5-15%.

Alternatively, other therapeutic agents as known to those in the field as useful to enhance the efficacy of the sling or reduce adverse reactions to the sling, for example, are contemplated with respect to the invention.

An exemplary method of making a sling 20 of the invention from a material, for example, includes manufacturing a sling material and forming a pattern of projections 40 on a portion of any, or all, edges 32, 34, 46 or 48 of the material. In one embodiment, the material of sling 20 is cut such that it has final maximum dimensions for placement in an anatomical site within the body. A pattern of projections 40 can be introduced along one or more edges 32, 34, 46 or 48 of the material.

The ends of the sling may terminate in any configuration or structure such as loops, apertures, male and female connectors, guide tubes and the like. Exemplary configurations and structures are disclosed in U.S. provisional patent application Ser. No. 60/403,555, U.S. provisional patent application Ser. No. 60/449,465, U.S. patent application Ser. No. 10/325,125, U.S. provisional patent application Ser. No. 60/418,827, U.S. provisional patent application Ser. No. 60/418,642, and U.S. provisional patent application Ser. No. 60/434,167, the entire contents of which are incorporated herein by reference.

The various illustrative slings described herein may be employed with any suitable sling delivery system. By way of example, the slings of the invention may be employed with any delivery systems appropriate for treating urinary incontinence. Such delivery systems include, for example, those delivery systems configured for supra-pubic, pre-pubic, transvaginal or transobturator approaches. Without limitation, exemplary delivery systems, methodologies, sling, sling attachments that may be employed can be found in U.S. patent application Ser. No. 10/460,112, U.S. patent application Ser. No. 10/093,498, U.S. patent application Ser. No. 09/916,983, U.S. patent application Ser. No. 10/093,398, U.S. patent application Ser. No. 10/093,450, U.S. patent application Ser. No. 10/094,371, U.S. patent application Ser. No. 10/092,872, U.S. patent application Ser. No. 09/916,983, U.S. provisional patent application Ser. No. 60/465,722, U.S. patent application Ser. No. 10/094,352, U.S. patent application Ser. No. 10/093,424, U.S. provisional patent application Ser. No. 60/403,555, U.S. provisional patent application Ser. No. 60/418,827, U.S. provisional patent application Ser. No. 60/418,642, U.S. provisional patent application Ser. No. 60/274,843, U.S. provisional patent application Ser. No. 60/286,863, U.S. provisional patent application Ser. No. 60/434,167, U.S. provisional patent application No. 60/495,439 entitled Surgical Slings, to Li, filed on even day herewith, U.S. patent application No. 10/641,942 entitled Medical Slings, to Chu, filed on even day herewith, U.S. patent application No. 10/641,487 entitled Systems, Methods and Devices relating to Delivery of Medical Implants, to Chu et al., filed on even day herewith, and U.S. patent application No. 10/640,838 entitled Medical Implant, to Chu et al., filed on even day herewith, the entire contents of which are incorporated herein by reference.

The sling 20 disclosed herein can be used to treat female urinary stress incontinence. Methods of sling delivery and implantation include but are not limited to tranvaginal, transabdominal, and transobturator procedures. In one embodiment, the sling 20 is placed inside the body of a patient such that the axis of the sling 20 that is perpendicular to the long axis of the sling parallels a portion of the mid-urethra. The sling 20 thereby provides a urethral platform limiting endopelvic fascia drop while providing compression to the urethral sphincter. The presence of the pattern of projections 40 on the sling 20 allow for the rapid vascularization and tissue ingrowth of the sling when it is placed in contact with the surrounding urethral and vaginal tissue.

Variations, modifications, and other implementations of what is described herein will occur to those of ordinary skill in the art without departing from the spirit and the scope of the invention. Accordingly, the invention is not to be limited by the preceding illustrative description.

What is claimed is:

1. A sling for implantation in a patient, comprising:
   a single piece of material having
      first and second transverse ends, and
      first and second longitudinal edges, wherein
         at least a portion of the first edge comprises a pattern of projections that extend laterally from the edge,
         a portion of the first edge on both sides of the a midpoint of a long axis of the sling is free of projections,
         at least one of the projections forms a laterally extending point which comprises at least two laterally extending, non-parallel sides, wherein the two sides form an angle of ninety degrees or less, and wherein
         the projections anchor the sling when the sling is implanted in the patient's tissues; and
      top and bottom surfaces comprising a pattern of ridges, wherein
         the ridges form at least one trough that extends continuously from the first edge to the second edge and terminates at the second edge, and wherein
         the pattern of ridges includes a ridge that has a different surface property than a surface property of a projection included in the pattern of projections; and
   a tensioning device, extending beyond at least one of the first and second ends of the piece of material.

2. The sling according to claim 1, comprising synthetic material.

3. The sling according to claim 1, comprising mammalian tissue.

4. The sling according to claim 1, comprising a combination of synthetic material and mammalian tissue material.

5. The sling according to claim 1, the second edge comprising a pattern of projections that extend laterally from the second edge.

6. The sling according to claim 1 wherein the top and bottom surfaces are circumscribed by the first and second ends and the first and second edges, wherein at least one of the top and bottom surfaces includes an irregular surface, and wherein the irregular surface anchors the sling when the sling is implanted in the patient's tissues.

7. The sling according to claim 1 comprising a substantially rectangular shape.

8. The sling according to claim 1, wherein the sling further comprises foam material.

9. The sling according to claim 1, wherein the pattern of projections is preselected.

10. The sling according to claim 1, wherein the sling further comprises a series of apertures extending from a first side to a second side of the material.

11. The sling of claim 10, wherein the sling includes a first end segment, a second end segment, and a middle segment, and wherein the plurality of apertures extends along at least one of the first end and the second end segments but not the middle segment.

12. The sling of claim 1, wherein the ridges extend laterally beyond the first edge of the material to form the pattern of projections.

13. The sling of claim 1, wherein the tensioning device is one of embedded into, intertwined with, woven into, molded to, and bonded to the sling.

14. The sling of claim 1, wherein the sling has a length, and the tensioning device extends along the length of the sling.

15. The sling according to claim 1, wherein at least one of the laterally extending projections is substantially V-shaped.

16. The sling according to claim 1, wherein each of the top and bottom surfaces comprises an irregular surface.

17. The sling according to claim 1, wherein the pattern of ridges includes a smooth curve and the pattern of projections includes a sharp angle.

18. The sling according to claim 1, wherein the pattern of projections is divided into lateral and medial sections spaced by a gap.

19. The sling according to claim 1, wherein the pattern of ridges includes at least a first peak and the pattern of projections includes at least a second peak, and wherein the first and second peaks are offset along the first or second longitudinal edge.

20. The sling according to claim 1, wherein the pattern of ridges includes a repeating element that is different from a repeating element included in the pattern of projections.

21. The sling according to claim 20, wherein the repeating element included in the pattern of ridges is a different shape than the repeating element included in the pattern of projections.

22. A method of making a sling for implantation in the tissues of a patient, the method comprising:
    providing a single piece of material including
        first and second transverse ends, and
        first and second longitudinal edges, and
        top and bottom surfaces circumscribed by the first and second ends and the first and second edges;
    introducing a pattern of projections into at least a portion of the first edge, the projections extending laterally from the first edge of the material with at least one of the projections forming a laterally extending point comprising at least two laterally extending, non-parallel sides, wherein the two sides form an angle of ninety degrees or less, and wherein a portion of the first edge on both sides of a midpoint of a long axis of the sling is free of projections;
    introducing an irregular surface property comprising a pattern of ridges into at least one of the top and bottom surfaces wherein the ridges to form at least one trough that extends continuously from the first edge and terminates at the second edge, and wherein the irregular surface property anchors the sling when the sling is implanted in the patient's tissues, and wherein the pattern of ridges includes a ridge that has a different surface property than a surface property of a projection included in the pattern of projections; and
    attaching a tensioning device to the material, wherein the tensioning device extends beyond at least one of the first and second ends of the piece of material.

23. The method of claim 22, wherein the material includes a pattern of projections introduced into at least a portion of the second edge, the projections extending laterally from the second edge of the material.

24. The method of claim 22, wherein the material comprises synthetic material.

25. The method of claim 22, wherein the material comprises mammalian tissue.

26. The method of claim 22, wherein the material comprises a combination of synthetic material and mammalian tissue.

27. The method of claim 22, wherein the material has a substantially rectangular shape.

28. The method of claim 22, further comprising introducing a plurality of apertures extending from a first side to a second side of the material.

29. The method of claim 28, wherein the sling includes a first end segment, a second end segment, and a middle segment, and the plurality of apertures is introduced along at least one of the first end and the second end segments but not the middle segment.

30. The method of claim 22, wherein the projections are preselected.

31. The method of claim 22, wherein the ridges extend laterally beyond the first edge of the material to form the pattern of projections.

32. The method of claim 22, wherein the tensioning device is one of embedded into, intertwined with, woven into, molded to, and bonded to the sling.

33. The method of claim 22, wherein the sling has a length, and the tensioning device extends along the length of the sling.

34. The method according to claim 22, wherein each of the top and bottom surfaces includes an irregular surface property.

35. The method according to claim 22, wherein at least one of the laterally extending projections is substantially V-shaped.

36. A sling for implantation in the tissues of a patient, comprising:
    a single piece of material including
        a first side and an opposing second side, and
        a perimeter edge that spans between the first and second sides, wherein the edge has an edge width and the first side has a side width and the edge width is less than the side width,
        a trough extending continuously along the side width, wherein
            at least one of the first and second sides has an undulating surface that is adapted to support an organ, and
            at least a portion of the edge includes a pattern of projections that extend laterally from the edge, with at least one of the projections forming a laterally extending point comprising at least two laterally extending, non-parallel sides, wherein the two sides form an angle of ninety degrees or less, and wherein the projections anchor the sling when the sling is implanted in the patient's tissues,
        a portion of the first edge on both sides of a midpoint of a long axis of the sling is free of projections, and
    a tensioning device.

37. The sling according to claim 36, wherein the undulating surface has undulations which extend orthogonally to the pattern of projections.

38. The sling according to claim 36, further comprising a surface having a pattern of ridges, wherein the ridges form the trough.

39. The sling according to claim 36, wherein the pattern of projections is preselected.

40. The sling of claim 36, wherein the single piece of material has first and second ends, and the tensioning device extends beyond at least one of the first and second ends.

41. The sling of claim 36, wherein the single piece of material extends in a first plane, and the pattern of projections extend laterally within the first plane.

42. The sling of claim 36, wherein the single piece of material extends in a first plane, and the undulating surface has undulations that extend out of the first plane.

* * * * *